United States Patent
Helvits et al.

(10) Patent No.: US 11,974,904 B2
(45) Date of Patent: May 7, 2024

(54) TAMPONS MADE OF NON-WOVEN FABRIC

(71) Applicant: ALBAAD MASSUOT YITZHAK LTD., Massuot Yitzhak (IL)

(72) Inventors: Shlomo Helvits, Pardes Hanna (IL); Chanan Yosef Adler, Jerusalem (IL)

(73) Assignee: ALBAAD MASSUOT YITZHAK LTD, Massuot Yitzhak (IL)

( * ) Notice: Subject to any disclaimer, the term of this patent is extended or adjusted under 35 U.S.C. 154(b) by 940 days.

(21) Appl. No.: 16/989,944

(22) Filed: Aug. 11, 2020

(65) Prior Publication Data
US 2022/0047428 A1    Feb. 17, 2022

(51) Int. Cl.
| | |
|---|---|
| *A61F 13/15* | (2006.01) |
| *A61F 13/20* | (2006.01) |
| *A61F 13/551* | (2006.01) |
| *A61L 15/28* | (2006.01) |
| *A61F 13/53* | (2006.01) |

(52) U.S. Cl.
CPC ...... *A61F 13/206* (2013.01); *A61F 13/15577* (2013.01); *A61F 13/2071* (2013.01); *A61F 13/55175* (2013.01); *A61L 15/28* (2013.01); *A61F 2013/15959* (2013.01); *A61F 2013/530029* (2013.01)

(58) Field of Classification Search
CPC .............. A61F 13/206; A61F 13/15577; A61F 13/2071; A61F 13/5517; A61F 2013/15959; A61F 2013/530029; A61L 15/28
See application file for complete search history.

(56) References Cited

U.S. PATENT DOCUMENTS

| | | | | |
|---|---|---|---|---|
| 5,807,372 | A | * | 9/1998 | Balzar ..................... A61F 13/34 604/385.18 |
| 6,740,070 | B2 | * | 5/2004 | Agyapong .............. A61F 13/34 604/385.18 |
| 2008/0200895 | A1 | * | 8/2008 | Minoguchi ....... A61F 13/15731 604/385.17 |
| 2011/0184367 | A1 | * | 7/2011 | Toms ................ A61F 13/55185 206/440 |
| 2020/0060883 | A1 | | 2/2020 | Font Caselles |

FOREIGN PATENT DOCUMENTS

EP         2749261        7/2014

* cited by examiner

*Primary Examiner* — Jacqueline F Stephens
(74) *Attorney, Agent, or Firm* — PEARL COHEN ZEDEK LATZER BARATZ LLP

(57) ABSTRACT

Tampons and production methods are provided that provide tampons made of at least 80% cellulose-based fibers, such as cotton or viscose, without plastic top sheets. The tampons consist of cylindrically-compressed rolled strips of entangled non-woven fabric and may be made of 100% natural cellulose-based fibers, the fabric having a tensile strength that is larger than 10N/50 mm. The fabric may be folded longitudinally in various folding configurations and rolled transversely before compression to tampon dimensions.

19 Claims, 10 Drawing Sheets

V-fold

C-fold

Double V-fold

Double C-fold

V-then-C fold

C-then-V fold

Double C-fold

Asymmetric Double C-fold

Z-fold

Z-then-C fold

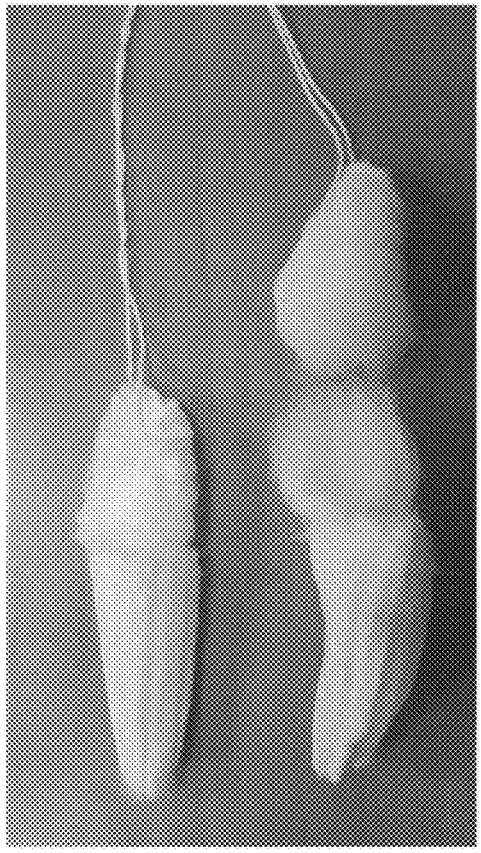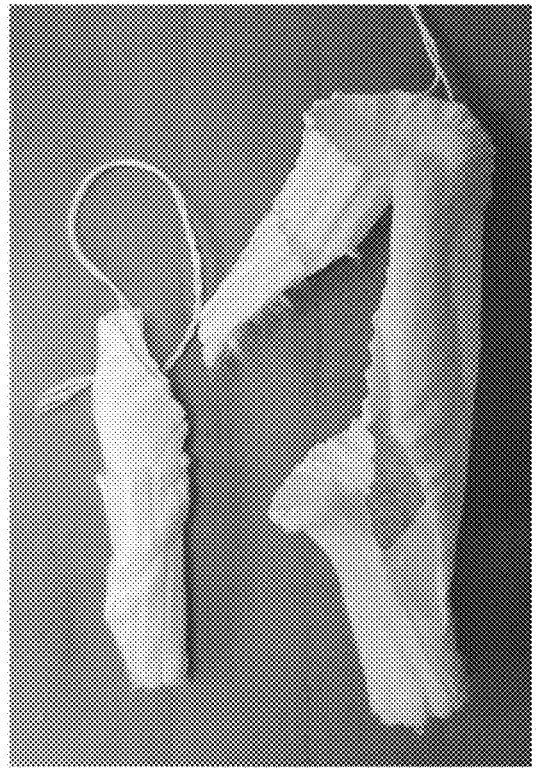
Figure 8B
Figure 8C
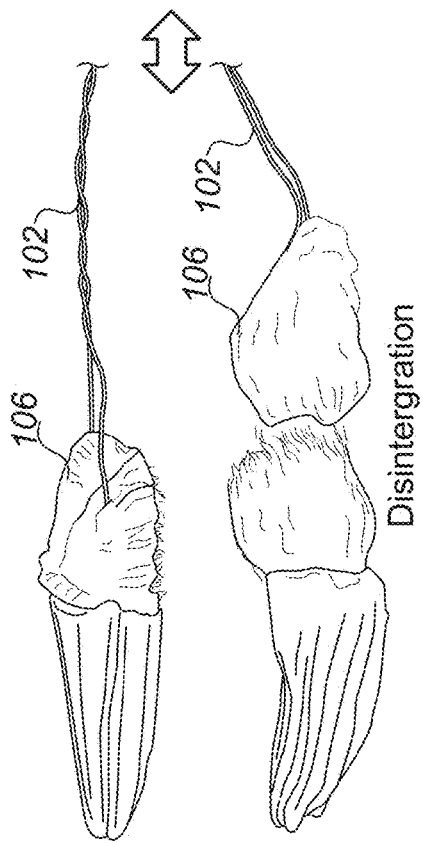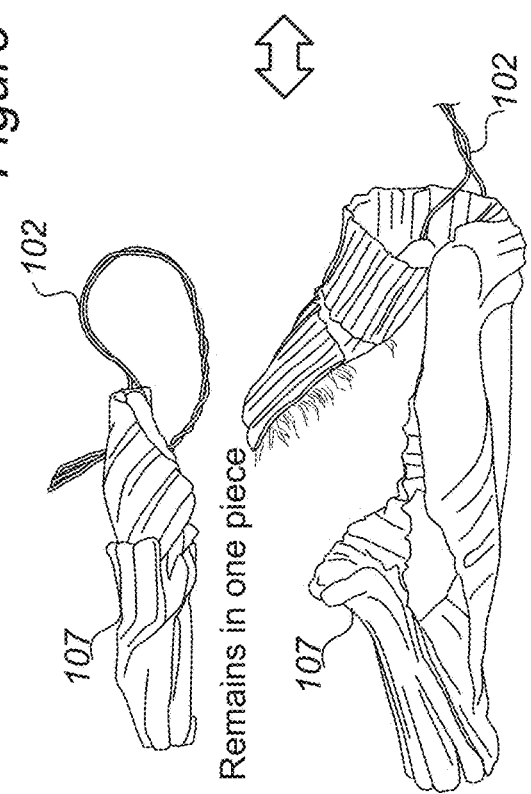

TAMPONS MADE OF NON-WOVEN FABRIC

BACKGROUND OF THE INVENTION

1. Technical Field

The present invention relates to the field of tampons, and more particularly, to top-sheet-free tampons.

2. Discussion of Related Art

European Patent Application No. 2749261, which is incorporated herein by reference in its entirety, discloses a catamenial tampon that includes a tampon body and a withdrawal string. The tampon body is composed of an absorbent material formed of a liquid-absorptive sponge and a wrapping material formed of a liquid-permeable sheet material and adapted to wrap the absorbent material.

U.S. Patent Application Publication No. 2020/0060883, which is incorporated herein by reference in its entirety, discloses a tampon, particularly for feminine hygiene, that comprises a substantially cylindrical absorbent body that is peripherally compressed and contained in a wrapper or in an applicator device. The absorbent body is formed by a rolled rectangular strip of absorbent material and comprises: a front end in the direction of insertion of the tampon, a rear end from which extends a removal string, and a lateral surface. The entirety of the outer surface of the absorbent body, corresponding to the front end, rear end and lateral surface is formed by a first layer of non-woven absorbent fabric.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a tampon consisting of a cylindrically-compressed rolled strip of entangled non-woven fabric made of at least 80% cellulose-based fibers, the fabric having a tensile strength that is larger than 10 N/50 mm.

One aspect of the present invention provides methods of preparing a tampon from entangled non-woven fabric alone, the methods comprising rolling a strip of entangled non-woven fabric made of at least 80% cellulose-based fibers, the fabric having a tensile strength that is larger than 10 N/50 mm, and cylindrically-compressing the rolled strip to specific tampon dimensions.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 8A-8C schematically illustrate a test for tampon integrity and its results for different types of tampons, illustrating the superior structural stability of the disclosed tampons, according to some embodiments of the invention.

DETAILED DESCRIPTION OF THE INVENTION

Figure 1A:
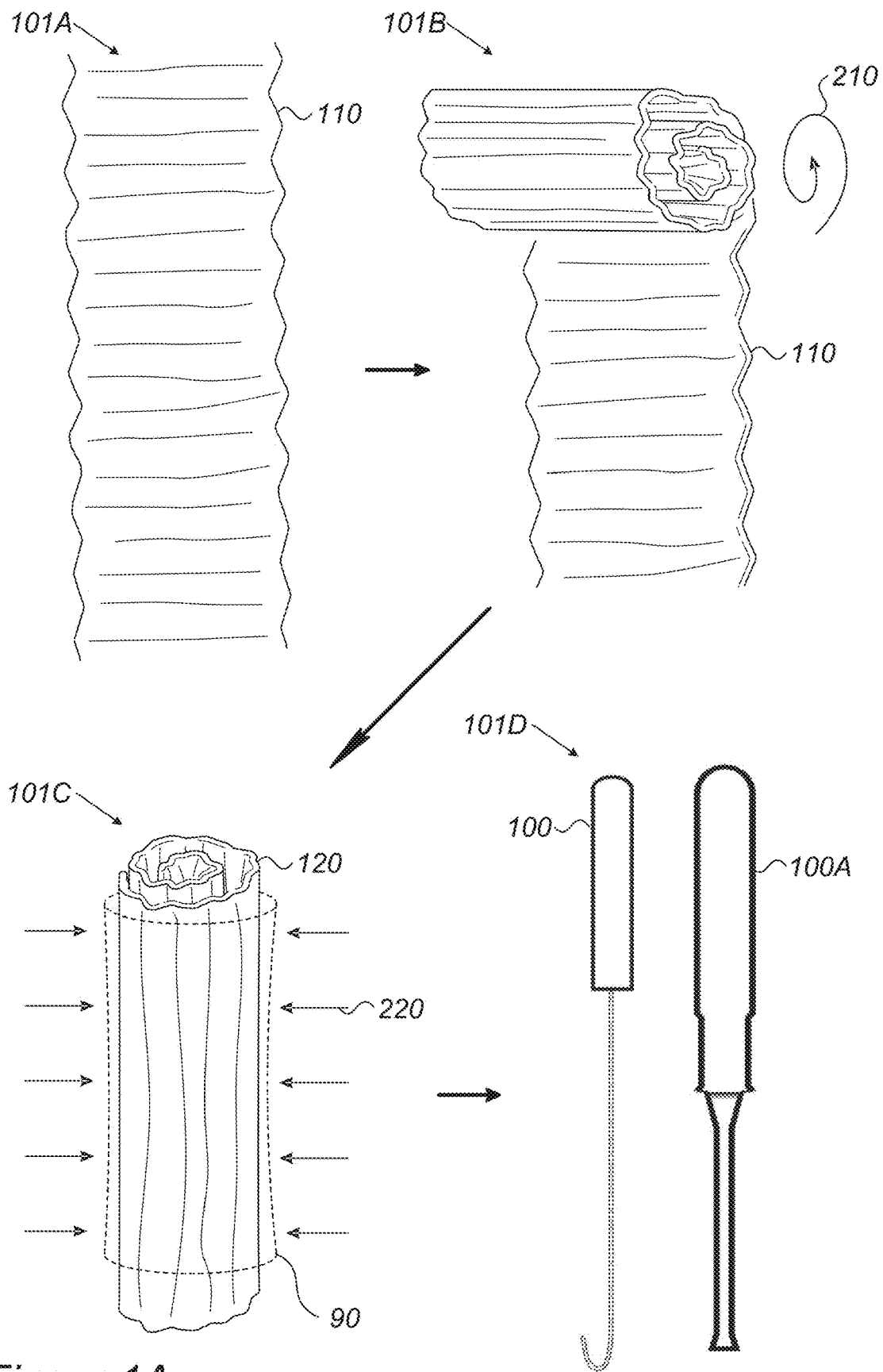
FIGS. 1A, 1B and 2-4 are high-level schematic illustrations of tampons and their preparation methods, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

A tampon is a fibrous, absorptive, generally cylindrical device having a front end for insertion into a vaginal cavity and a rear end opposite the front end. In the embodiments described herein, a strip of material is rolled, such that roll forms the diameter of the cylindrical device, while the transverse dimension of the strip (which may be folded prior to rolling as described below) forms the length of the device from end to end. Tampons have predetermined dimensions of length and diameter which, as practiced in the art, may vary within known ranges, established according to the user's size, preference, quantity of catamenial flow, and other factors.

Embodiments of the present invention provide efficient and economical methods for producing tampons. Tampons and production methods are provided that provide tampons made of at least 80% cellulose-based fibers. Cellulose-based fibers are fibers made from natural cellulose or from modified cellulose, such as cotton or viscose, respectively, and equivalent materials. A finished tampon having at least 80% cellulose-based fibers is provided without a plastic top sheet. The tampons consist of cylindrically-compressed rolled strips of entangled non-woven fabric made of at least 80% cellulose-based fibers, the fabric having a tensile strength that is larger than 10 N/50 mm. The fabric may be folded longitudinally in various folding configurations (folding types), and rolled transversely before compression to predetermined tampon dimensions. Disclosed tampons are much stronger than prior art tampons due to the higher tensile strength of the non-woven fabric (>10 N/50 mm of the non-woven fabric versus <5 N/50 mm for prior art tampons) and due to the optional folding of the non-woven fabric as explained below. Disclosed tampons may be produced from entangled non-woven fabric such as hydro-entangled spunlace non-wovens or needle-punch entangled non-wovens, or from other types of non-wovens that are characterized by sufficient tensile strength (e.g., >10 N/50 mm).

FIGS. 1A, 1B and 2-4 are high-level schematic illustrations of tampons 100 and their preparation methods 200, according to some embodiments of the invention. FIGS. 5A-5J are high-level schematic illustrations of non-limiting examples for folding types of the strip, prior to rolling the folded strip to prepare a tampon therefrom, according to some embodiments of the invention. FIGS. 6A-6D are high-level schematic illustrations of non-limiting examples for rolling various folding types to prepare a tampon therefrom, according to some embodiments of the invention. FIGS. 6E-6G are high-level schematic illustrations of non-limiting examples of rolled and compressed tampons, according to some embodiments of the invention. Elements from FIGS. 1A, 1B, 2-4, 5A-5J and 6A-6G may be combined in any operable combination, and the illustration of certain elements in certain figures and not in others merely serves an explanatory purpose and is non-limiting. FIG. 7 is a high-level flowchart illustrating a method 200 of preparing tampons according to some embodiments of the invention. The method stages may be carried out with respect to tampons 100, which may be optionally configured to be prepared by method 200. Method 200 may comprise the following stages, irrespective of their order, unless expressly stated otherwise.

Tampons 100 may be configured as digital tampons (inserted by finger) or applicator tampons (inserted by an applicator) as illustrated schematically in FIG. 1A (stage 101A). Tampons 100 may consist of a compressed rolled strip 110 of non-woven fabric, possibly being made of at least 80% cellulose-based fibers, such as cotton or modified cellulosic fibers, such as viscose, without any plastic top sheet. In certain embodiments, strip 110 may be made of spunlace (hydro-entangled) non-woven fabric, which holds its shape after compression—to replace the prior art solution of using the top sheet for this purpose.

Disclosed methods 200 of preparing tampons only from non-woven fabric and a removal string (stage 201) may comprise associating a removal string with a fabric strip so that it is anchored in the tampon after rolling the strip (stage 202), rolling the strip of non-woven fabric (stage 210) and compressing and forming the rolled strip to specific tampon dimensions (stage 220). Method 200 may further comprise packaging the tampon (and optionally attaching an applicator to the tampon) (stage 230). It is noted that compression reduces tampon diameter about two-fold, from typical widths of 20-35 mm down to 10-17 mm, depending on the type of tampon (see, e.g., Table 1 for types). The inventors have noted that tampons 100 maintain their shape and dimensions following compression 220.

FIG. 1A illustrates schematically stage 101A of preparing strip 110 of non-woven fabric, stage 101B of rolling (stage 210) strip 110, stage 101C of compressing and forming (stage 220) rolled strip 120 and stage 101D of preparing tampons 110 from the compressed rolled strips, including, e.g., packaging (for digital tampons) and/or associating the tampon with an applicator and packaging (for applicator tampons). It is noted that certain embodiments comprise packaged tampons 100. Prior art tampons typically include a top sheet 90 (shown in broken lines and not part of disclosed tampons 100) that envelopes rolled material at least partly, and is sealed by heat application during the compression stage. However, in disclosed tampons 100 no top sheet 90 is used.

Figure 1B:
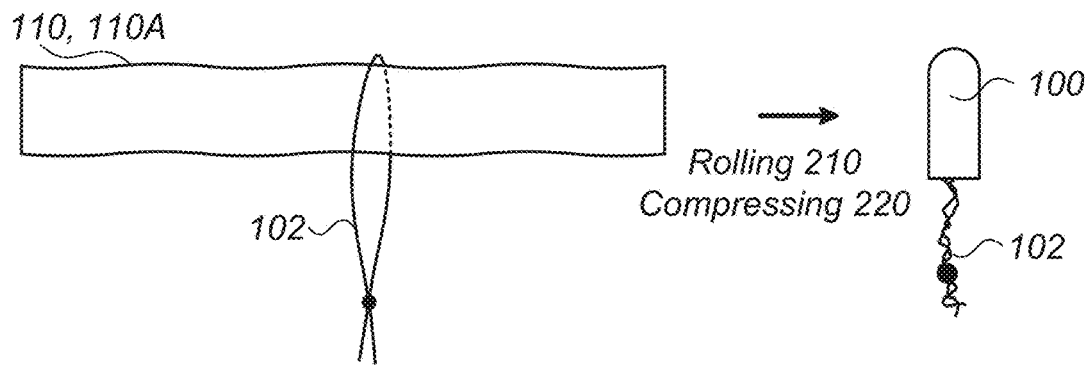

FIG. 1B illustrates schematically the incorporation of a string (removal string or cord, made of at least 80% cotton) 102 into tampon 100 for disclosed tampons 100, according to some embodiments of the invention. Removal string 102 may be folded around strip 100 and/or around folded strip 110A (and its ends attached. e.g., tied together) before rolling 210 is carried out. After rolling 210, string 102 is safely anchored within the rolled strip and can be used to extract tampon 100 following use.

In certain embodiments, method 200 may comprise folding the strip longitudinally before the rolling thereof transversely (stage 205). In certain embodiments, method 200 may comprise folding and rolling the strip to leave exposed fabric edge(s) (stage 215), as explained below. In certain embodiments, method 200 further comprises mechanically or hydro-entangling cotton and/or viscose fibers to form an elongated strip (stage 180) and feeding the elongated strip to a continuous folding and/or rolling operation to form a tampon without a body facing topsheet (stage 190).

Figure 2:
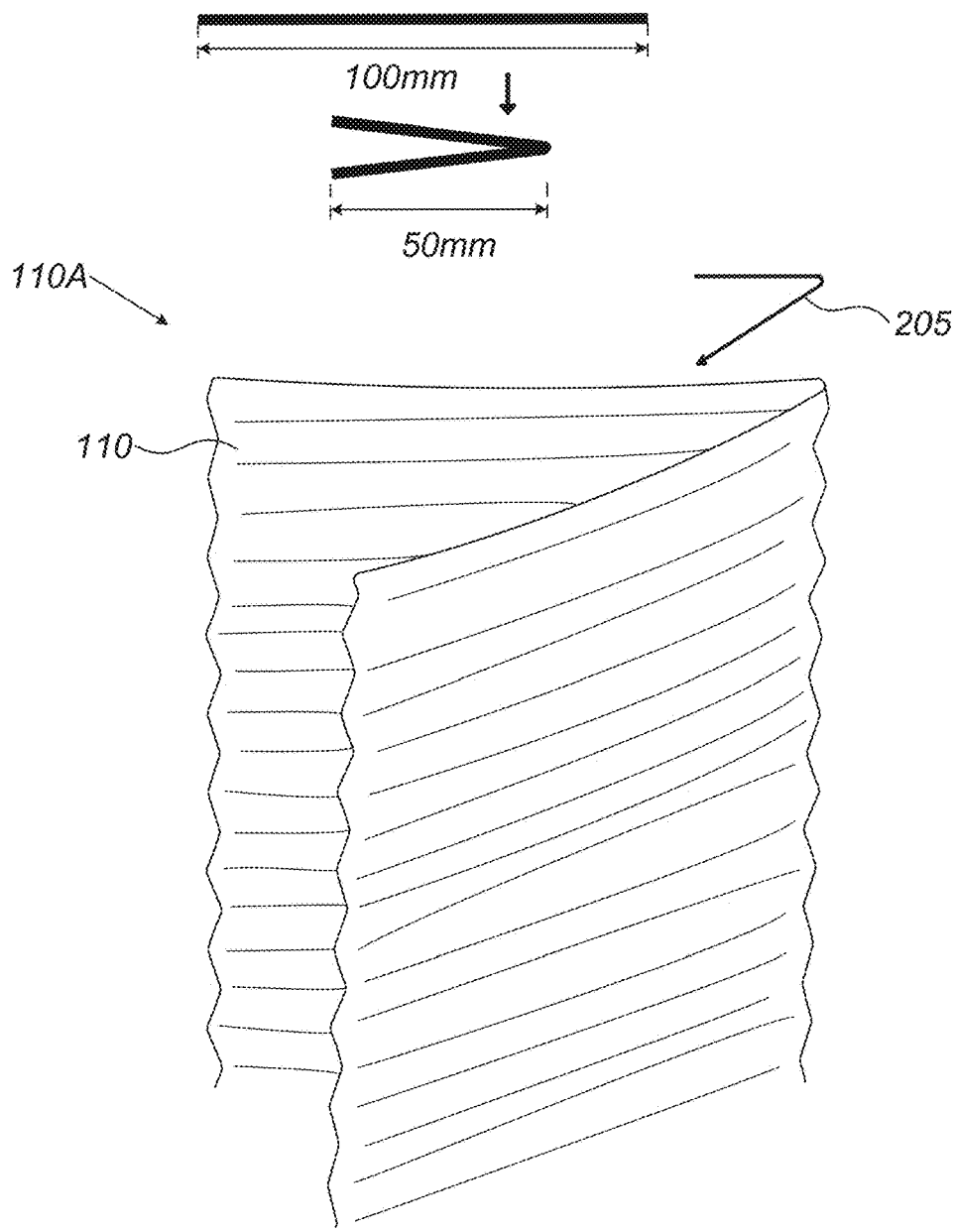
Figure 3:
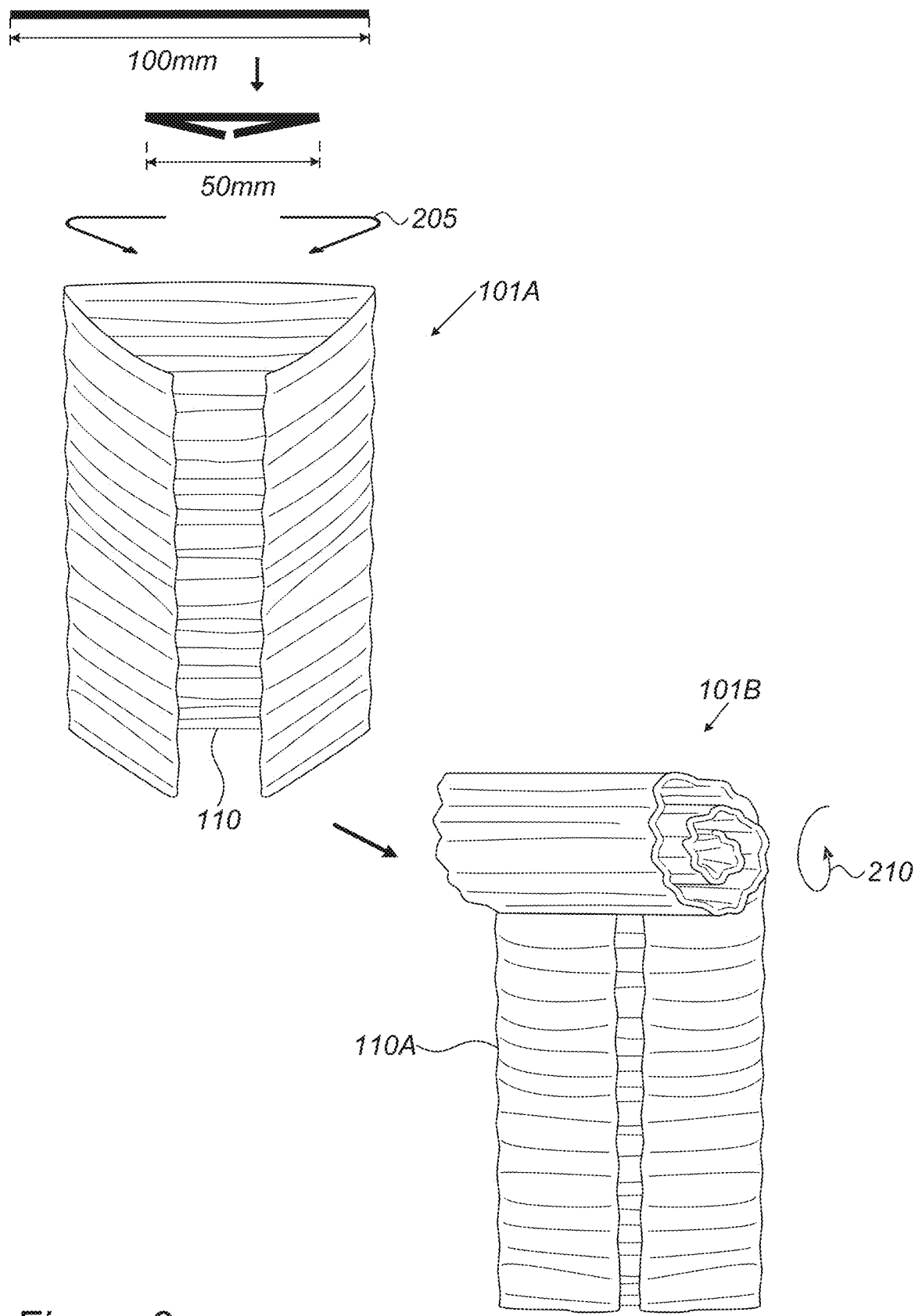
Figure 4:
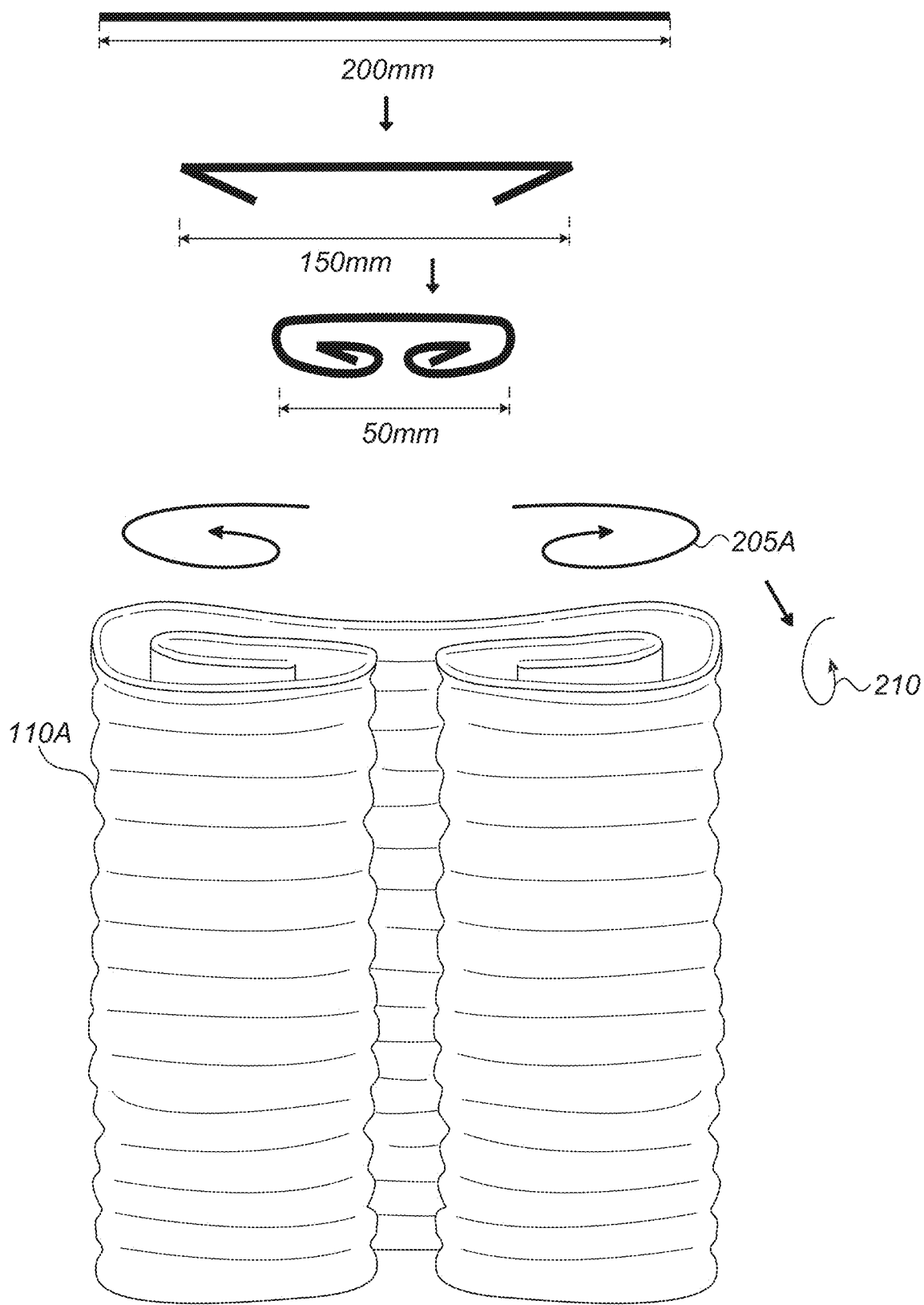

As illustrated schematically in FIGS. 2-4, tampons 100 may be made of strips 110 that are folded longitudinally (stage 205) before the rolling thereof transversely (210). For example, as illustrated schematically in FIG. 2, strip 110 may be folded longitudinally centrally (with a central longitudinal fold) to half the width of strip 110 and rolled (as strip 110A) transversely. This type of fold is termed herein "V-fold".

In certain embodiments, as illustrated schematically in FIGS. 3 and 4, strip 110 may be folded longitudinally along one or more lateral (side) folds. For example, as illustrated schematically in FIG. 3, strip 110 may be folded (205) longitudinally along two lateral (side) longitudinal folds—to half the width of strip 110 (stage 101A) and rolled (as strip 110A) transversely (stage 101B). This type of fold is termed herein "C-fold".

In another example, as illustrated schematically in FIG. 4, strip 110 may be folded (205A) longitudinally along two lateral double side longitudinal folds (two consecutive C-folds)—to quarter the width of strip 110 and the rolled (as strip 110A) transversely (stage 210 as illustrated schematically in FIGS. 1-3). This type of fold is termed herein "double C-fold". It is noted that in practice, a double-C fold may be achieved by two (or possibly three) consecutive folds as illustrated schematically in FIGS. 4 and 5G below.

In various embodiments, as explained in detail below, strip 100 may be folded longitudinally and folded strip 110A may be rolled transversely—for example, strip 110A maybe folded longitudinally applying at least one of a C-fold, a V-fold and a Z-fold—reducing the strip width by a factor of 2 or 3; and/or strip 110A maybe folded longitudinally applying at least two consecutive folding types, each selected from a C-fold, a V-fold and a Z-fold—reducing the strip width by a factor of 2, 3.4 or 6; possibly the longitudinal fold may be asymmetric, and the width reduction factor may be any factor determined by initial strip width and required tampon length (typically 50 mm). For example, initial widths of strips 110 may be 50 mm, 100 mm, 150 mm, 200 mm or any other width, and strip 110 may be folded to a width that corresponds to the length of tampon 100 (e.g., 50 mm). Folded strip 110A may be rolled and compressed to form tampon 100.

FIGS. 5A-5J are high-level schematic illustrations of non-limiting examples for folding (205) types of strip 100, which may be used to prepare strip 110A to be rolled (210) and compressed into tampon 100. It is noted that the measures indicated in the figures are non-limiting and approximate, and are merely intended to show in a general way the variation in strip width and the schematic effects of folding the strip on the resulting strip width.

Figure 5A:
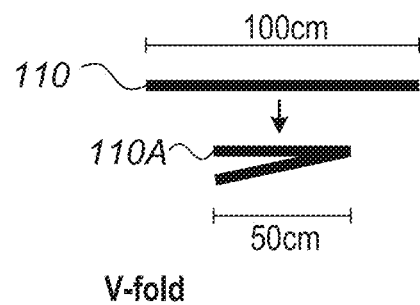
FIGS. 5A-5J are high-level schematic illustrations of non-limiting examples for folding types of the strip, prior to rolling the folded strip to prepare a tampon therefrom, according to some embodiments of the invention.
Figure 5B:
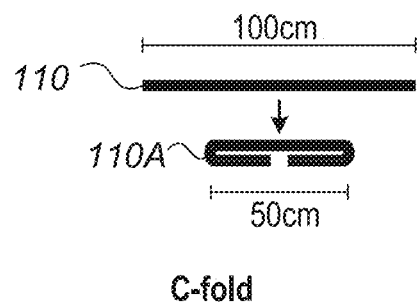
Figure 5C:
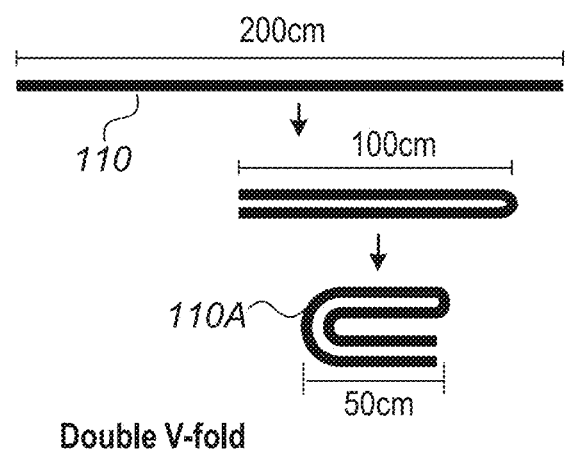
Figure 5D:
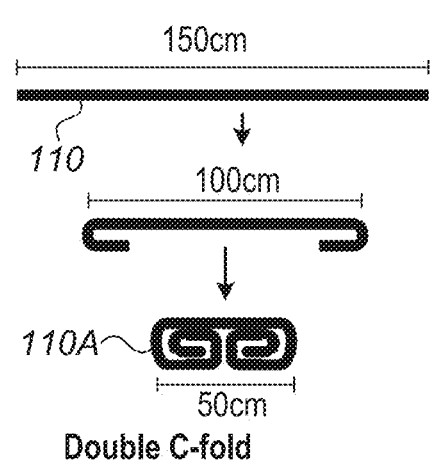

FIG. 5A illustrates schematically a V-fold folding type (as also illustrated schematically in FIG. 2); FIG. 5C illustrates schematically a double-V-fold (two consecutive V-folds) folding type; FIG. 5B illustrates schematically a C-fold folding type (as also illustrated schematically in FIG. 3); FIG. 5D illustrates schematically a double-C-fold folding type (two consecutive C-folds, as also illustrated schematically in FIG. 4). FIG. 5G illustrates schematically a double-C-fold of a different folding type, in which the first C-fold is C-folded at side lines in already-folded strip parts (other than the double-C-fold of FIG. 5D in which the strip ends are in effect rolled).

Figure 5E:
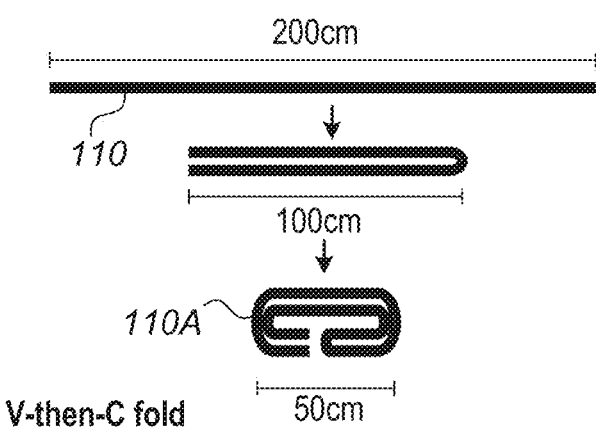
Figure 5F:
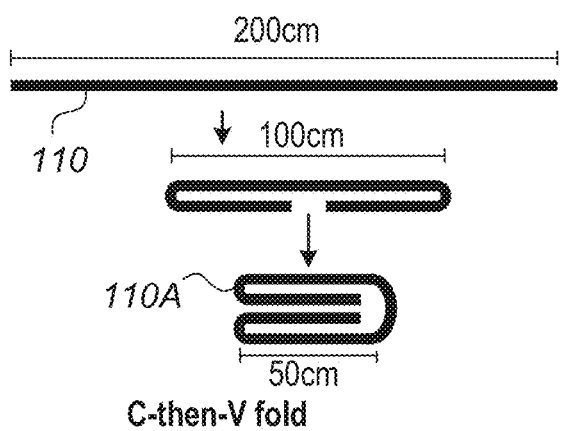
Figure 5G:
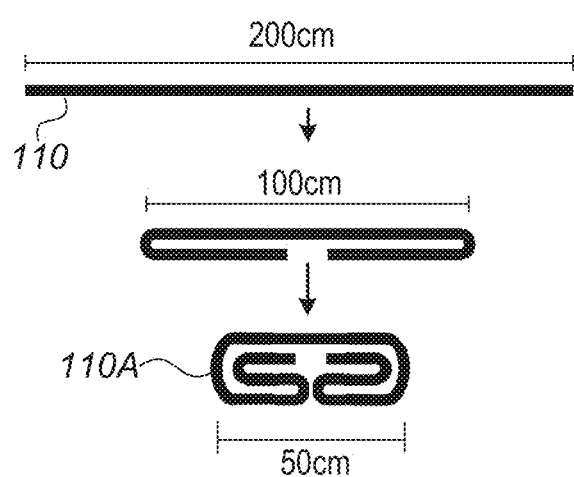
Figure 5H:
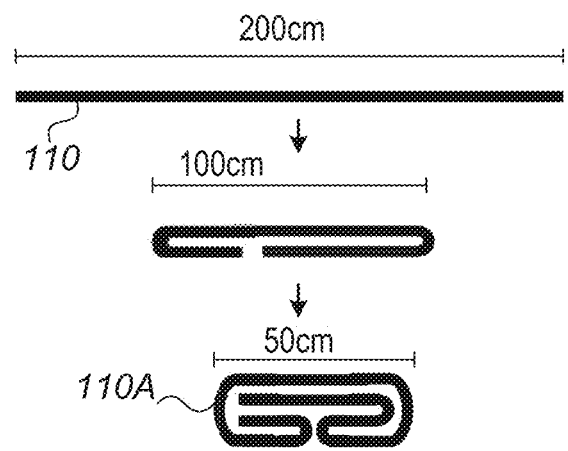
Figure 5I:
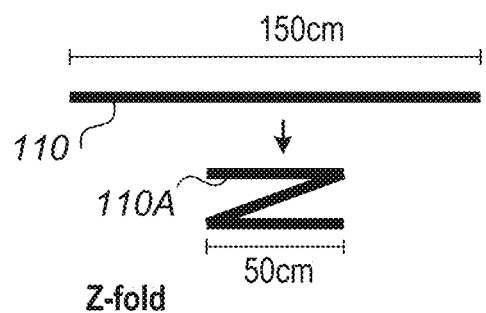
Figure 5J:
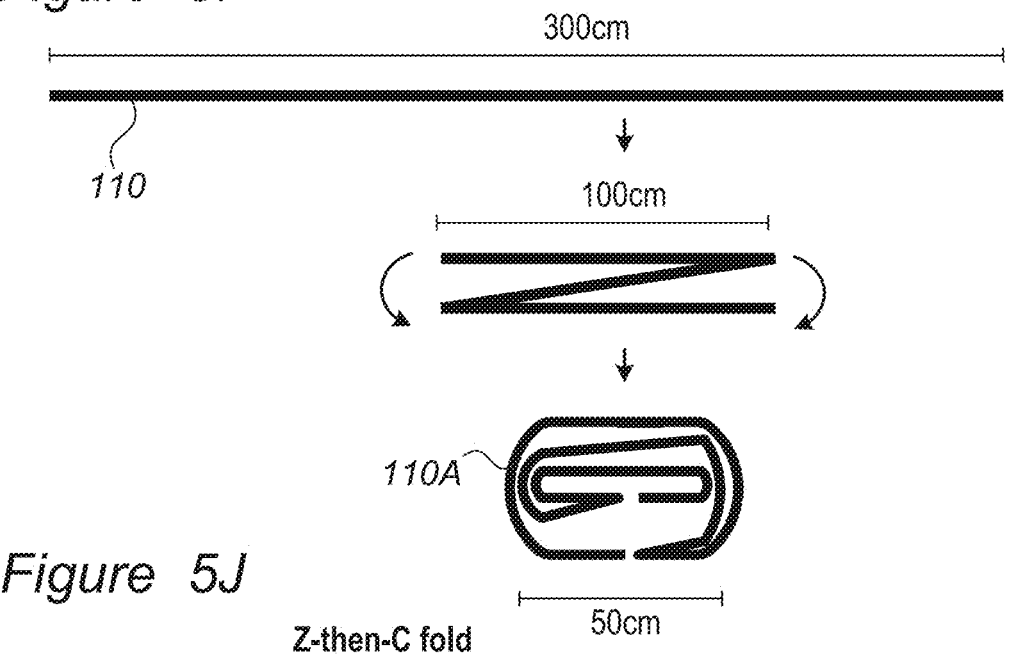

FIG. 5E illustrates schematically a V-then-C fold (V-fold followed by C-fold) folding type; and FIG. 5F illustrates schematically a C-then-V fold (C-fold followed by V-fold) folding type. FIG. 5I illustrates schematically a Z-fold folding type (folding into three layers instead of two layers in V-fold and C-fold) and FIG. 5J illustrates schematically a Z-then-C-fold folding type (a Z-fold followed by a C-fold). It is noted that these are non-limiting examples, and that various combinations of V-fold, C-fold and Z-fold may be used to fold strip 100 into strip 110A which is then rolled (210) and compressed (220) to form tampon 100 (including, e.g., longitudinal pressing to form the dome-shaped front end of tampon 100 and set the tampon length).

The various folding types may be selected with respect to various parameters such as the width of strip 100, structural stability of tampon 100 to withstand specified tensile strains (see below), integrity of tampon 100, prevention of loose fabric fibers at the ends of tampon 100 (the ends of tampon 100 are formed from the rolled sides of each folding pattern as the folding is longitudinal and the rolling is transversal), and so forth. Multiple (more than two) consecutive folds may also be used, either of one type (e.g., triple-V-fold), or of two or more types (e.g., V-then-Z-then-C-fold or any other combination). Any of the folding types may be asymmetric, as illustrated schematically in FIG. 5H for an asymmetric-double-C-fold, in which in the first and second C-folds the sides are different in their length, forming a complementary fold that prevents a possibility of the central lines in the symmetric C-folds to overlap each other and form a weak region in the tampon rolled from the folded strip.

In certain embodiments, strip 110 and/or folded strip 110A may be rolled to prevent exposure of free fabric edges (seams) in the prepared tampon, or tampon 100 may be configured to have exposed fabric edges (seams) at a middle section or end thereof, as explained in detail below. In this context, "exposed" means on an outer surface (e.g., a body facing surface) of the tampon.

Figure 6A:
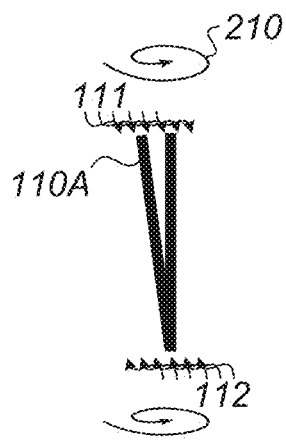
FIGS. 6A-6D are high-level schematic illustrations of non-limiting examples for rolling various folding types to prepare a tampon therefrom, according to some embodiments of the invention.
Figure 6B:
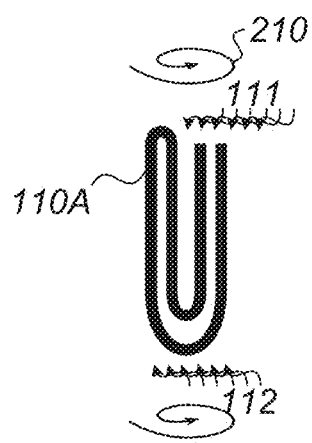
Figure 6C:
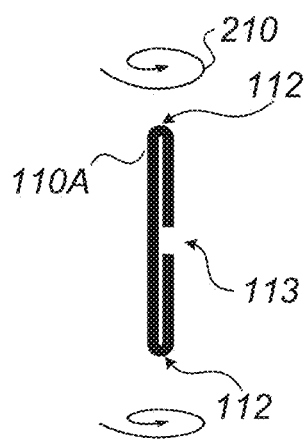
Figure 6D:
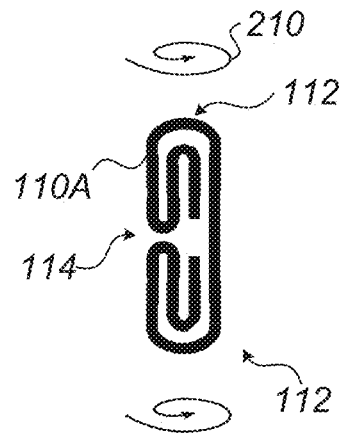
Figure 6E:
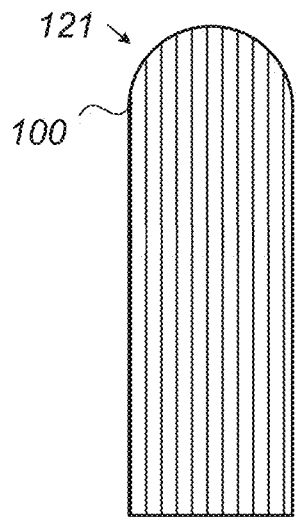
FIGS. 6E-6G are high-level schematic illustrations of non-limiting examples of rolled and compressed tampons, according to some embodiments of the invention.
Figure 6F:
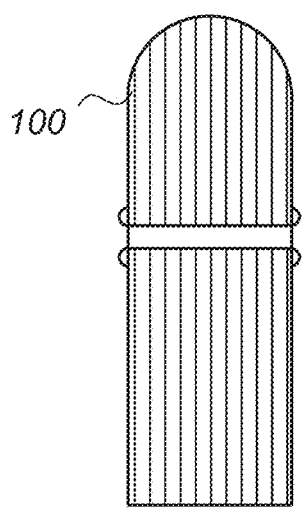
Figure 6G:
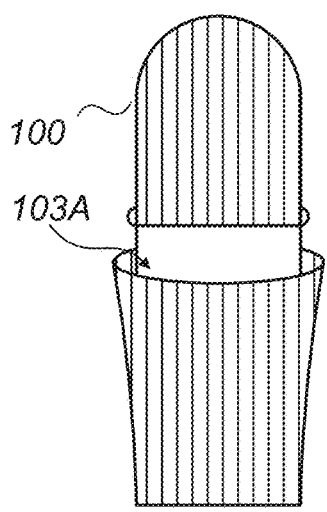
Figure 7:
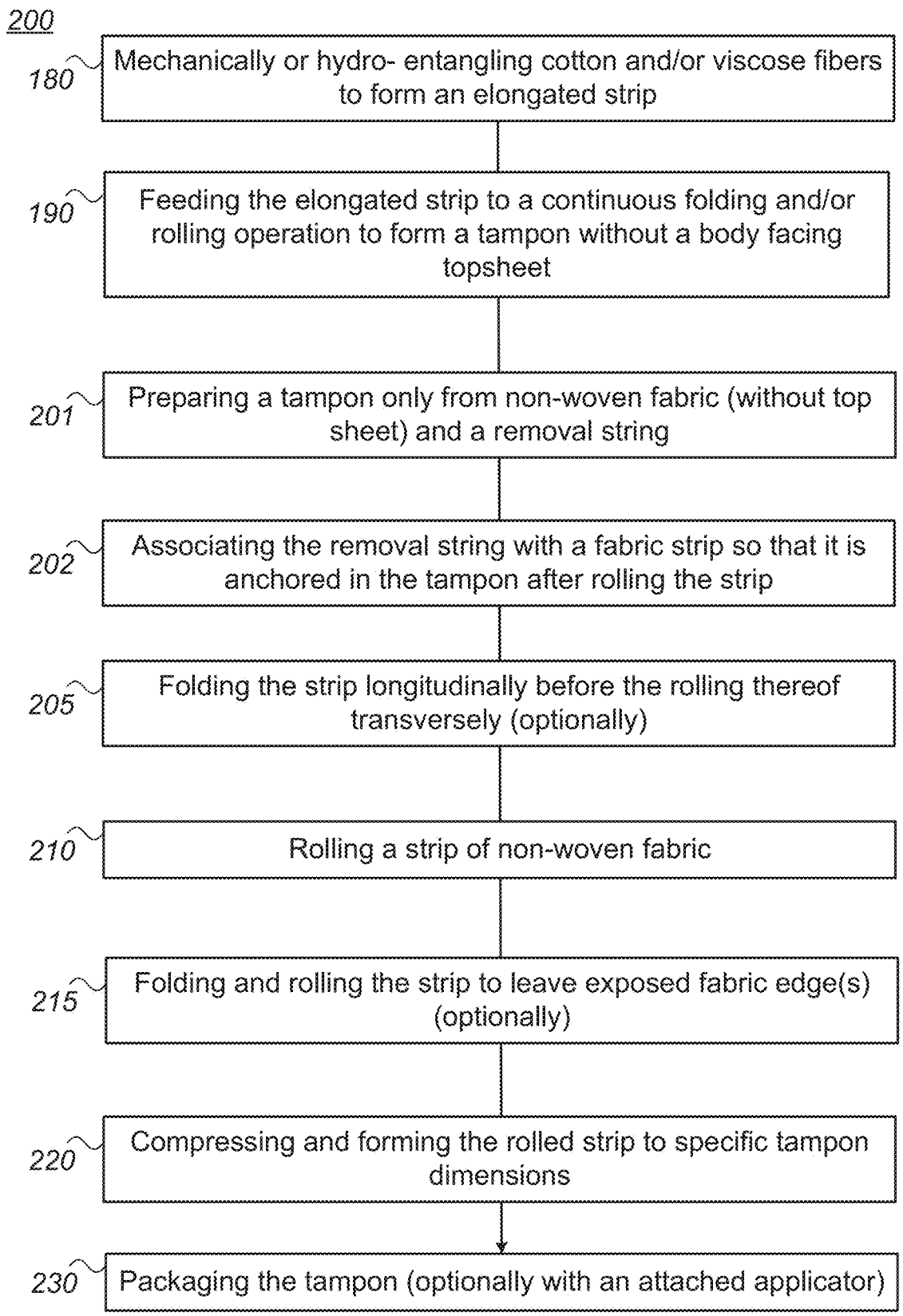
FIG. 7 is a high-level flowchart illustrating methods of preparing tampons according to some embodiments of the invention.

FIGS. 6A-6D are high-level schematic illustrations of non-limiting examples for rolling (210) of various folding types of folded strip 110A, to prepare tampon 100 therefrom, according to some embodiments of the invention. FIGS. 6A and 6B illustrate, respectively, rolling of V-folded and double-V-folded strips 110A, resulting in one side of prepared tampon 100 with edges 111 of strip 100 (indicated schematically by arrows) and in the other side of prepared tampon 100 with folds 112 of strip 100 (indicated schematically by arrows). As illustrated schematically in FIGS. 6C and 6D, strip 100 may be folded to position fabric edges 113 and/or fold edges 114 (respectively) at the center (or off-center, when the folding type is asymmetric) of strip 110A. In some embodiments, folding may be carried out asymmetrically to avoid overlapping of fabric edged 113 and/or of fold edges 114 over multiply-rolled layers. In some embodiments, rolling 210 may be carried out to cover fabric edged 113 and/or of fold edges 114 by the other side of continuous fabric (as illustrated schematically in FIG. 6C). In some embodiments, rolling 210 may be carried out to expose fabric edged 113 and/or of fold edges 114 and rolling the other side of continuous fabric internally (as illustrated schematically in FIG. 6D).

FIGS. 6E-6G are high-level schematic illustrations of non-limiting examples of rolled and compressed tampons 100, according to some embodiments of the invention. In FIG. 6E, a front (leading, proximal) end 121 and a back (following, distal) end 122 of tampon 100 are indicated. It is noted that in various embodiments, either front or back end 121, 122, respectively, may be configured to correspond with wither of the sides of rolled strip 110A, and therefore either front or back end 121, 122, respectively, may be configured to comprise of rolled and compressed edges 111 of strip 100 and/or to comprise of rolled and compressed folds 112 of strip 100, depending on specified design requirements. In FIG. 6F, tampon 100 is schematically illustrated with a central or off-centered gap 103 formed by fabric edges (exposed at a middle section of tampon 100) resulting from the folding type of strip 100, as explained above. Gap 103 may be designed to enhance absorption by tampon 100, by allowing fluid to enter the tampon structure through a relatively free fabric edge 103A that accommodates fluids into tampon 100. Configurations of fabric edges at e.g., at front end 121 of tampon 100 may be left exposed (at the front and/or rear end of tampon 100) and used for enhancing absorption (e.g., upon rolling V-folded strips 110A as illustrated, e.g., in FIGS. 6A and 6B). In some embodiments, avoiding fabric edges at front end 121 and/or avoiding gaps 103 may be preferred in tampon design and preparation to enhance the structural integrity of tampon 100. Any of these design choices are enabled herein by the corresponding folding types (and in relation to the rolling direction).

As illustrated schematically in stage 101C in FIG. 1, compressing 220 may be carried out cylindrically to entangle the fibers from the rolled non-woven fabric, in order to maintain the compressed shape and dimensions of the rolled strip. For example, compression 220 may be carried out by simultaneous rotation of multiple members position around the circumference of the tampon. The inventors have found out that using non-woven fabric (e.g., made of 80%, 90% or 100% cellulose-based fibers, such as cotton or viscose), possibly folded and then rolled prior to compression, yields tampons with a stable structure, possibly due to the mechanical characteristics of the non-woven fabric. As a result, stable compressed tampons made of 80%, 90% or 100% cellulose-based fibers (e.g., entangled non-woven fabric, such as hydro-entangled or mechanically-entangled fabric) may be produced, which enable dismissing of the prior art plastic top sheet (prior art tampons typically have a plastic top sheet that holds the tampon material together and is made e.g., of polypropylene, polyethylene and/or polyester). In certain embodiments, disclosed method and tampon configurations provide tampons 100 which are made of 100% cellulose-based fibers such as cotton and/or viscose. It is noted that entanglement in various forms enhances the tensile strength of the non-woven fabric by entangling the fibers in the fabric. For example, entanglement may increase the tensile strength of the non-woven fabric above 10 N/50 mm.

In non-limiting examples, taking the tampon length as about 50 mm, the width of strip 110 may be ca. 50 mm when rolled without prior folding, as illustrated schematically in FIG. 1, the width of strip 110 may be ca. 100 mm when rolled with prior folding as illustrated schematically in FIGS. 2 and 3, or the width of strip 110 may be ca. 200 mm when rolled with prior double-folding, as illustrated schematically in FIG. 4—as indicated schematically by the cross-sectional details in the respective figures. As shown in FIGS. 5A-5J, a wide range of folding types and initial strip width may be combined and used to reach a required final tampon length (corresponding to the width of folded strip 110) with specified strength requirements. It is noted that a value modified by the term "about" or "ca." is understood to encompass ±10% of the value.

Typically, disclosed non-woven fabrics are between 25-150 gr/m$^2$, and a few (e.g., 1-3) mm thick. Non-woven fabric material of strip 110 may comprise spunlaced (hydro-entangled) cotton fibers and/or viscose fibers. For example, cotton fibers may have 1.1 to 2.3 dtex (dtex is defined as the fiber weight in grams per 10 km) and be 10-30 mm long. Viscose fibers may have 2.4-3.5 dtex and be 30-40 mm long. The cotton fibers and viscose fibers may be used at any weight ratio. In various embodiments, non-woven fabric material may comprise natural pulp fibers and/or cellulose fibers in addition or in place of some of the cotton and/or cellulose fibers. In certain embodiments, tampons 100 may be made of 80%, 85%, 90% or 95% cellulose-based fibers (or any intermediate value), with the rest of the fabric fibers being synthetic, while maintaining the required tampon absorption capacity. Non-limiting examples for synthetic fibers include any combination of polyethylene, polypropylene, polyester or equivalent materials, including bi-component synthetic fibers. Advantageously, high cellulose fiber content, up to 100%, may be achieved in disclosed embodiments that do not require top sheets.

In various embodiments, the fabric weight may be between 30-130 gsm (gr/cm$^2$). Typical values of the tensile strength of the fabric are larger than 10 N/50 mm, and may reach, e.g., MD (machine direction) values of 11, 15, 30, 35, 40, 45 N/50 mm, or intermediate or higher values. Strip 110 of the fabric may be surface bonded—treated or configured to prevent fiber linting. It is noted that the tensile strength data refer to measurement standard in which the maximal force (in N) is measured for tearing a 50 mm wide strip of fabric (hence the notation N/50 mm refers to the force in N measured on a 50 mm wide strip). MD and CD tensile strengths were measured according to ISO 9073-3 (Test methods for nonwovens-part 3); Test pieces were cut to 50 mM±0.5 mm wide and of sufficient length. The tests are carried out in a standard atmosphere. A constant rate of extension of 200 mm/min was applied. For measuring values of wet samples, the cut pieces were impregnated with 200% (weight) water. The force curve was used to determine the tensile strength values.

Figure 8A:
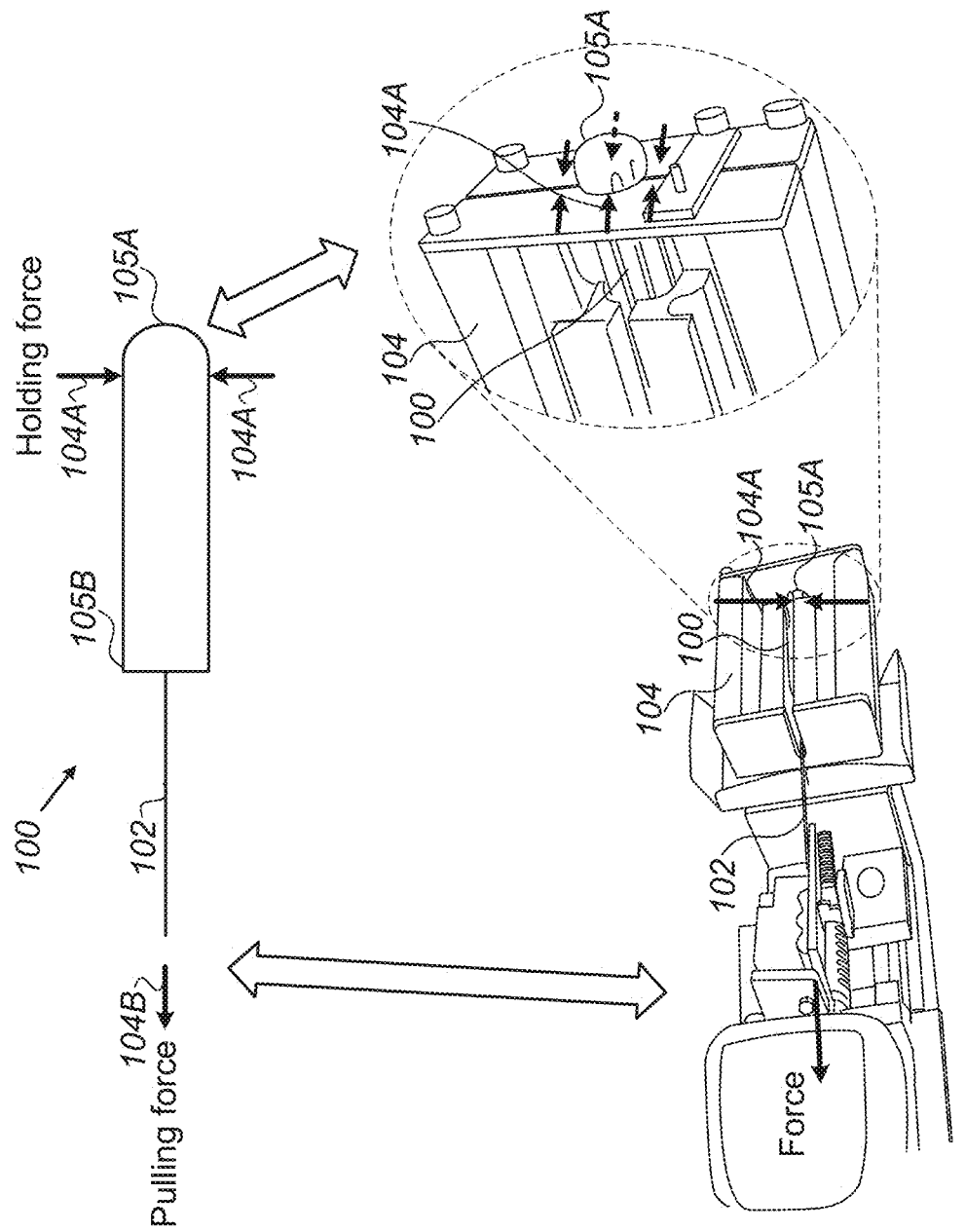

FIGS. 8A-8C schematically illustrate a test for tampon integrity and its results for different types of tampons, illustrating the superior structural stability of disclosed tampons 100, according to some embodiments of the invention. In the test, illustrated schematically in FIG. 8A, a front end 105A of tampon 100 is held tightly in a clamp 104 (applying a holding force 104A, clamp 104 shown in FIG. 8A in top view and enlarged in side view) and then string 102 is pulled at a gradually increasing and measured pulling force 104B until the tampon gives way to the pulling, typically by disintegrating at its rear end 105B. The threshold pulling force 104B at which disintegration starts is referred to below as the tampon unravelling force.

FIG. 8B illustrates test results for applied forces beyond the unraveling force—showing disintegration and tearing 106 of tampon material in prior art tampons made of weakly attached fibers. Upon pulling out such tampons, loosely attached fibers may remain in the body, or even parts of the tampon may disintegrate and remain in the body.

FIG. 8C illustrates test results for applied forces beyond the unraveling force—showing that disclosed tampons 100 remain in one piece, maintaining structural integrity 107 and fibers of the non-woven fabric of which tampons 100 are made. Folded and rolled fabric layers may be pulled out of the tampon structure but are not torn or disintegrated—allowing complete extraction of the tampon material even under extreme use conditions.

Accordingly, not only do disclosed tampons 100 provide much higher strengths (having higher unraveling force than prior art tampons, as shown in Table 1), but are also much safer in case applied higher forces damage the tampon structure (as shown in FIG. 8C).

Table 1 provides unraveling force measurements from 24 tests, comparing the unraveling force of disclosed tampons 100 (double-C folded and rolled non-woven) to the unraveling force of prior art tampons (cotton-based, with thermoplastic top sheet), in three tampon categories. It is noted that disclosed tampons 100 may be produced in any of these or other categories. Typical absorption performance (absorbency rating) for "regular" tampons is 6-9 gr, for "super" tampons is 9-12 gr and for "super plus" tampons is 12-15 gr. Disclosed tampons 100 have been found to have similar absorption performance to prior art tampons in these three categories.

TABLE 1

Experimental comparison of the unraveling force for prior art and disclosed tampons.

| Category Tampon type/ | Regular | | Super | | Super plus |
|---|---|---|---|---|---|
| Unraveling force (N) | Prior art | Disclosed tampons | Prior art | Disclosed tampons | Disclosed tampons |
| Average | 31.6 | 41.4 | 28.9 | 40.6 | 56.3 |
| Standard deviation | 8.5 | 13.0 | 14.6 | 9.8 | 12.6 |
| Minimum | 21.0 | 24.8 | 11.9 | 23.4 | 26.8 |

In both Regular and Super tests, $p < 0.005$ in Student's t-test. In the Super plus test, data for prior art tampons was not available.

It is noted that the inventors have found out that not only are disclosed tampons 100 stronger and have a stabler structure than prior art tampons, but also that their form of disintegration is safer. While in prior art tampons the cotton material at the rear end breaks apart and may be separated from a front part of the torn tampon, disclosed tampons 100 maintain structural continuity even after disintegration, with strip 110 unraveling but maintaining its integrity without breaking apart from the front part of the tampon. Advantageously, this difference further enhances the safety of disclosed tampons 100, allowing complete removal of the used tampon from the body, even if it gets unraveled.

Advantageously, disclosed tampons 100 provide several advantages over prior art tampons. First, disclosed tampons 100 may be made of 100% natural cellulose-based fibers, such as cotton or viscose, in contrast to prior art tampons that require a plastic-based top sheet to maintain the integrity of the tampon, and in contrast to prior art tampons that pose a risk of disintegration and/or may leave residual fibers within the body. It is noted that prior art top sheets come in direct contact with the body, and removing them in disclosed tampons 100 cause the body contact to be with cotton. Second, the high tensile strength of the fabric used to form disclosed tampons 100 and the optional folding of the fabric cause disclosed tampons 100 to have an integral and stable structure, which is not found in prior art attempts to produce 100% cotton tampons. In such attempts, prior art tampons exhibit low structural integrity which may cause disintegration of the tampon upon removal leaving behind cotton fibers or lumps that pose danger of infection. In contrast, disclosed tampons 100 are much stronger, no not rupture upon large tensile strains and do not have loose fibers that can be left behind in the body.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A tampon consisting of a cylindrically-compressed rolled strip of entangled non-woven fabric and an attached removal string, wherein the fabric is made of at least 80% cellulose-based fibers, and has a tensile strength that is larger than 10 N/50 mm, wherein the rolled strip comprises a longitudinally double-C-folded strip that is rolled transversely.

2. The tampon of claim 1, wherein the longitudinal double C fold is asymmetric.

3. The tampon of claim 1, wherein the strip is folded longitudinally to reduce a width of a starting strip of entangled nonwoven fabric by a width reduction factor of 2, 3, or 4.

4. The tampon of claim 1, wherein the rolled strip is free of exposed free fabric edges in the tampon.

5. The tampon of claim 1, having exposed fabric edges at a middle section of the tampon.

6. The tampon of claim 1, wherein the non-woven fabric is hydro-entangled spunlace non-woven fabric or needle-punched non-woven fabric.

7. The tampon of claim 1, wherein the nonwoven fabric consists of cotton and/or viscose fibers.

8. The tampon of claim 1, wherein the fabric is made of 100% cellulose-based fibers.

9. A packaged tampon comprising the tampon of claim 1.

10. A method of preparing a tampon from entangled non-woven fabric alone, the method comprising:
    folding longitudinally in a double-C-fold an elongated strip of entangled non-woven fabric with an attached removal string, wherein the fabric is made of at least 80% cellulose-based fibers and has a tensile strength that is larger than 10 N/50 mm,
    transversely rolling the longitudinally double-C-folded strip, and
    cylindrically compressing the rolled strip to predetermined tampon dimensions.

11. The method of claim 10, wherein the longitudinal double C folding is asymmetric.

12. The method of claim 10, wherein the non-woven fabric is hydro-entangled spunlace non-woven fabric or needle-punched non-woven fabric.

13. The method of claim 10, comprising mechanically entangling cotton and/or viscose fibers to form an elongated strip and feeding the elongated strip to a continuous folding and/or rolling operation.

14. The method of claim 10, wherein the fabric is made of 100% cellulose-based fibers.

15. The method of claim 10, wherein the longitudinal folding reduces a width of a starting strip of entangled nonwoven fabric by a width reduction factor of 2, 3, or 4.

16. The method of claim 10, wherein the longitudinal folding is configured to make the rolled strip free of exposed free fabric edges in the tampon.

17. The method of claim 10, wherein the longitudinal folding is configured to keep exposed fabric edges at a middle section of the tampon.

18. The method of claim 10, wherein the nonwoven fabric consists of cotton and/or viscose fibers.

19. The method of claim 10, further comprising packaging the tampon.

* * * * *